(12) United States Patent
Cavanaugh et al.

(10) Patent No.: US 9,038,552 B1
(45) Date of Patent: May 26, 2015

(54) METHOD TO USE A PHOTOLUMINESCENT ADJUVANT IN AGRICULTURAL APPLICATIONS

(75) Inventors: Kevin Cavanaugh, Collierville, TN (US); Timothy B. Cartwright, Germantown, TN (US)

(73) Assignee: Floratine Products Group, Inc, Collierville, TN (US)

( * ) Notice: Subject to any disclaimer, the term of this patent is extended or adjusted under 35 U.S.C. 154(b) by 259 days.

(21) Appl. No.: 13/559,491

(22) Filed: Jul. 26, 2012

Related U.S. Application Data

(60) Provisional application No. 61/512,795, filed on Jul. 28, 2011, provisional application No. 61/514,205, filed on Aug. 2, 2011, provisional application No. 61/525,879, filed on Aug. 22, 2011, provisional application No. 61/525,876, filed on Aug. 22, 2011, provisional application No. 61/549,300, filed on Oct. 20, 2011, provisional application No. 61/549,304, filed on Oct. 20, 2011, provisional application No. 61/557,527, filed on Nov. 9, 2011, provisional application No. 61/591,125, filed on Jan. 26, 2012.

(51) Int. Cl.
*A01C 1/00* (2006.01)
*A01N 43/90* (2006.01)
*A01M 7/00* (2006.01)

(52) U.S. Cl.
CPC .............. *A01N 43/90* (2013.01); *A01M 7/0092* (2013.01)

(58) Field of Classification Search
USPC ................ 47/57.6, 58.1 LS, 58.1 R, 1.5, 1.7; 118/300; 111/127, 7.4, 118
See application file for complete search history.

(56) References Cited

U.S. PATENT DOCUMENTS

| | | | | |
|---|---|---|---|---|
| 3,653,550 | A * | 4/1972 | Williams | 222/136 |
| 4,683,826 | A * | 8/1987 | Solie et al. | 111/124 |
| 5,575,111 | A * | 11/1996 | Rajamannan | 47/58.1 R |
| 5,946,851 | A * | 9/1999 | Adey et al. | 47/1.5 |
| 6,202,346 | B1 * | 3/2001 | Lyons et al. | 47/57.6 |
| 6,298,598 | B1 * | 10/2001 | Wach et al. | 47/1.1 |
| 6,566,477 | B2 * | 5/2003 | Sanders et al. | 526/321 |
| 6,689,609 | B1 * | 2/2004 | Fan et al. | 435/422 |
| 6,989,056 | B2 * | 1/2006 | Babler | 106/413 |
| 6,990,913 | B2 * | 1/2006 | Pedrazzoli | 111/200 |
| 2001/0022047 | A1 * | 9/2001 | Krysiak et al. | 47/58.1 |
| 2004/0128908 | A1 * | 7/2004 | Neumann | 47/57.6 |
| 2008/0250710 | A1 * | 10/2008 | Hirasawa et al. | 47/58.1 LS |
| 2009/0229177 | A1 * | 9/2009 | Hyde et al. | 47/1.7 |
| 2011/0296750 | A1 * | 12/2011 | Davis | 47/1.7 |

* cited by examiner

*Primary Examiner* — Rob Swiatek
*Assistant Examiner* — Morgan T Barlow
(74) *Attorney, Agent, or Firm* — Harris, Shelton, Hanover & Walsh; Susan B. Fentress

(57) ABSTRACT

The invention provides a non-toxic photoluminescent adjuvant delivered to targeted crops, plants and seeds to assist spray operations in low light or dark light operations. These crops and plants include: not for human consumption crops, turf grass, ornamental flowers, seeds, shrubs and bushes. Spray operations are delivered to the foliar, crown and soil parts and seeds of a crop or plant.

7 Claims, 5 Drawing Sheets

US 9,038,552 B1

METHOD TO USE A PHOTOLUMINESCENT ADJUVANT IN AGRICULTURAL APPLICATIONS

RELATED APPLICATIONS

Figure 1:
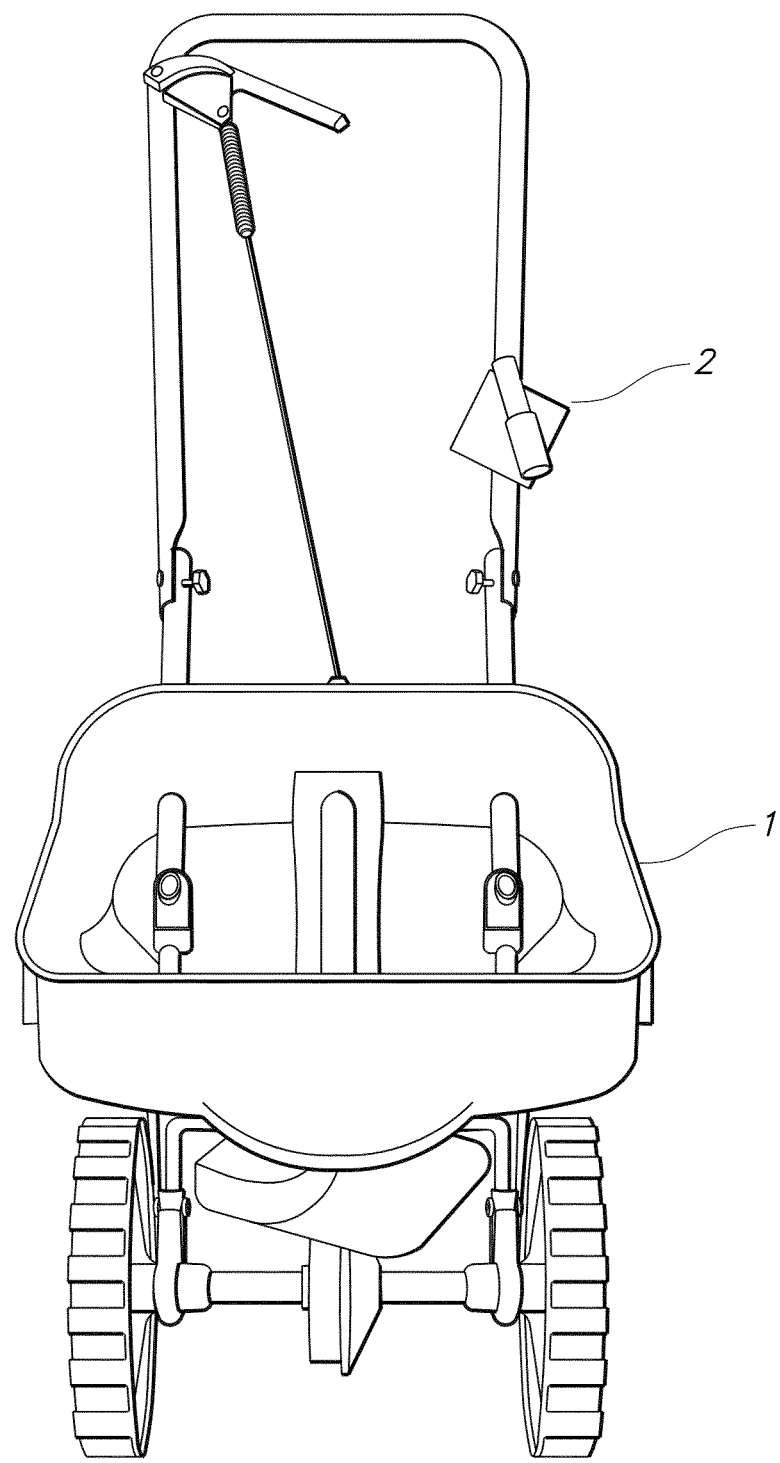
Figure 2A:
Figure 2B:
Figure 2C:
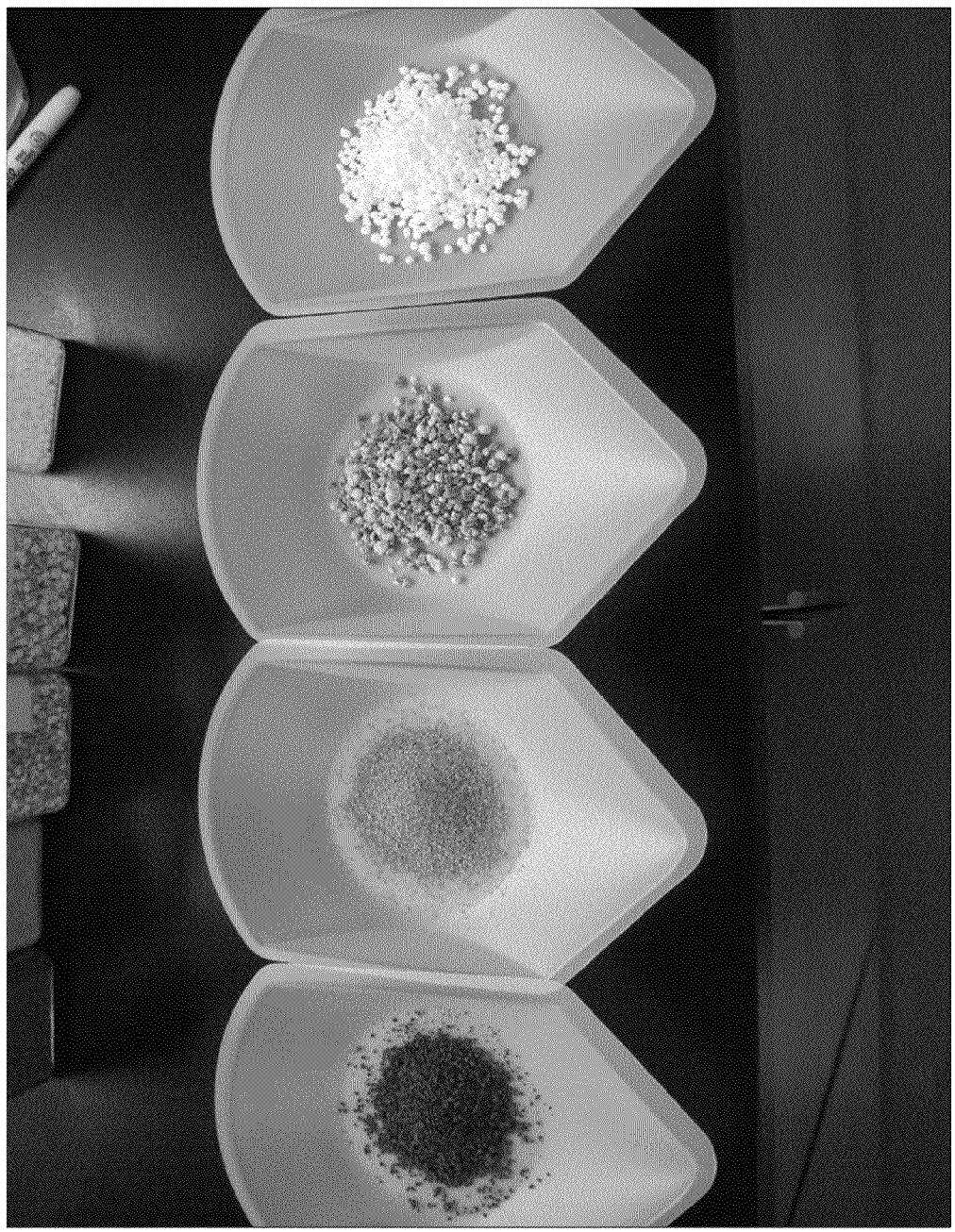
Figure 2D:

This application claims the benefit of: U.S. Application Ser. No. 61/512,795, filed Jul. 28, 2011; U.S. Application Ser. No. 61/514,205, filed Aug. 2, 2011; U.S. Application Ser. No. 61/525,879 filed Aug. 22, 2011; U.S. Application Ser. No. 61/525,876 filed Aug. 22, 2011; U.S. Application Ser. No. 61/549,300, filed Oct. 20, 2011; U.S. Application Ser. No. 61/549,304, filed Oct. 20, 2011; U.S. Application Ser. No. 61/557,527, filed Nov. 9, 2011; and U.S. Application Ser. No. 61/591,125 filed Jan. 26, 2012, under 35 U.S.C. 119(e), hereby specifically incorporated by reference in their entirety.

FIELD OF THE INVENTION

This invention is directed to a method to use a photoluminescent adjuvant to assist in agricultural applications.

BACKGROUND OF THE INVENTION

The act of applying chemicals, pesticides, nutrients, biostimulants, water solubles, watering agents and water to plants through spray applications is not new. Spraying materials by means of water or other liquid carrier in aqueous solution for broadcast applications to plants and crops is known in the art. Adjuvants are commonly used to improve the performance of a plant modulator performance. One classification of adjuvants is spray dye marker indicators which assists spray operations by visually notifying the operator by means of coloration or darkening of the intended or unintended target to the presence of an application of spray mixture. These spray dye marker indicators provide limited uses during spraying operations as they require daylight or artificial (non-backlight) light for visual verification of the spray mixture.

SUMMARY OF THE INVENTION

This invention is related to a method for the incorporation of photoluminescent materials to be sprayed on to and into plants, seeds and soils. The product assists the spray operator through the use of black lights allowing for precise night time spray and seeding operations. More specifically, this invention relates to a photoluminescent adjuvant to be applied to targeted crops, plants and seeds to assist in the night-time application of bioactive agents, such as chemicals and pesticides. The photoluminescent adjuvant can be applied as a solution, foam spray or as a dry granular material.

In another embodiment, this invention relates to a method to assist spray operation in low light or dark light operations. The method includes the steps of mixing a photoluminescent adjuvant with a liquid based active ingredient to form a solution and then applying the solution to targets crops, plants and seeds in low light or dark light operations. In one embodiment, the solution is applied with the aid of a black light. In another embodiment, the photoluminescent adjuvant is mixed with a surfactant, to form a solubilized adjuvant.

In another embodiment, this invention also relates to a method to control delivery of dry formulated active ingredients to assist in low light or dark light operations. The method includes the steps of: sparging a photoluminescent adjuvant with dry granular material including an active ingredient, to provide a photoluminescent adjuvant coated material; and delivering the photoluminescent adjuvant coated materials in low light or dark light conditions to a desired target area.

BRIEF DESCRIPTION OF THE SEVERAL VIEWS OF THE DRAWING

For a fuller understanding of the nature and desired objects of the present invention, reference is made to the following detailed description taken in conjunction with the accompanying drawing figures.

FIG. 1 shows a black light mounted to a sprayer.

FIG. 2A shows a black and white photograph of an embodiment of the invention.

FIG. 2B shows a black and white photograph of an embodiment of the invention.

FIG. 2C shows a black and white photograph of an embodiment of the invention.

FIG. 2D shows a black and white photograph of an embodiment of the invention.

DETAILED DESCRIPTION OF THE INVENTION

The present invention may be understood more readily by reference to the following detailed description of the invention. It is to be understood that this invention is not limited to the specific devices, methods, conditions or parameters described herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of preferred embodiments of the inventions, and are not restrictive of the invention as claimed.

In one embodiment, the use of photoluminescent materials for foliar and soil spray applications is for the absorption by plants, seeds or soils and allows for the intended spray application to be administered and applied with the use of ultraviolet light. These crops and plants include: not for human consumption crops, turf grass, ornamental flowers, seeds, soils, shrubs and bushes. Spray operations are delivered to the foliar, crown and soil parts of a crop or plant.

The present invention relates to the controlled delivery of chemicals, pesticides, nutrients, biostimulants, water solubles, wetting agents and water to plants, seeds and soils with the incorporation of a photoluminescent adjuvant designed for assisting spray operations.

Photoluminescence is a process in which a substance absorbs photons (electromagnetic radiation) and then re-radiates photons. There are two types of photoluminescence.

Fluorescence is light energy produced by a process where high-energy radiation (such as ultraviolet or X-ray) is absorbed by electrons surrounding an atom and is re-emitted as light energy. Phosphorescence is light energy produced by a particular type of chemical reaction where the excess chemical energy of the reactants is given off as light energy.

The photoluminescent adjuvant is mixed with a liquid bioactive active agent, such as chemicals, pesticides, nutrients, biostimulants, water solubles, wetting agents and water to plant parts or its soil. It is the unique nature of this formulation that allows for the absorption into plant tissues for its intended purpose(s).

The photoluminescent adjuvant in this embodiment is made of a nontoxic optical brightener. This optical brightener may be made of cellulous or other nontoxic ingredients. One example of a nontoxic optical brightener is Keyfluor™ (Keystone Laboratories).

The photoluminescent adjuvant is mixed within a spray solution prior to application of the intended target. Through the use of the photoluminescence the total adjuvant solution can be applied in low light or dark light conditions through the use of mounted black light or lights ensuring precision spray to the targeted area. The experimentation showed that the optimum inclusion rate of the adjuvant was about 0.2% w/w with a maximum of 0.4% w/w depending on the opacity of the active ingredients. The amount of active ingredients ranged from 10% w/w to 25% w/w.

In an alternative embodiment, the photoluminescent adjuvant is delivered to the intended target via foam. In this embodiment, the photoluminescence adjuvant is mixed with a surfactant in a container under pressure; the solubilized adjuvant is dispensed from the container via an applicator and forms foam upon contact with the environment.

Now referring to FIG. 1, a mobile apparatus 1 to dispense the active ingredient is used to apply the photoluminescent adjuvant with a solution or dry pellet containing an active agent to plants, such as turf grass. The spreader 1, includes a black light 2 mounted on the spreader 1. Under ultraviolet light, the photoluminescence adjuvant allows the operator precise control of the spray mixture and nozzle performance across the boom which is better than in traditional daylight operations with spray dye indicators.1

Example 1

Treatment: Plots were hand sprayed daily for one week. The solution contained 2% by volume of OB (optical brightness) solution in water. The nontoxic optical brightener in this example is Keyfluor™ (Keystone Laboratories). Soil samples and tissue samples taken next day, as shown in Table 1. The only significant difference in the data is seen in the tissue Na levels with a 5× increase from 0.06 to 0.3. These measurements showed Na at 0.3% in tissue. This is "High" but no acute effects were seen in the plants. Additionally, there appeared to be slight discoloration of the plants, as a result of the treatment.

TABLE 1

| Soil Sample | NH4 + NO3 | PO4 | K | Ca | Na | Fe | B |
|---|---|---|---|---|---|---|---|
| Pre-Treatment | 0.8 | 0.13 | 0.34 | 0.6 | 0.62 | 58 | 0.3 |
| Post Treatment | 1.8 | 0.10 | 0.28 | 0.8 | 0.78 | 9 | 0.1 |

TABLE 1-continued

| Tissue Sample | Total N | P | K | Ca | Na | Fe | B |
|---|---|---|---|---|---|---|---|
| Pre-Treatment | 1.3 | 0.25 | 1.4 | 0.4 | 0.06 | 248 | 15 |
| Post Treatment | 1.5 | 0.30 | 1.5 | 0.4 | 0.3 | 340 | 27 |

In another embodiment, photoluminescent materials incorporated into granular applications can be used to assist operator ensuring accuracy and precision of the granular substance(s) during low light or night-time operations.

This embodiment relates to the controlled delivery of dry formulated active ingredients, such as, chemicals, pesticides, nutrients, biostimulants, granular fertilizers, and other dry substances to be administered to plants or soils with the incorporation of a photoluminescent material for accurate dissemination to the intended target.

The adjuvant is a nontoxic optical brightener. In this example the photoluminescent adjuvant is Keyfluor™ (Keystone Laboratories). The adjuvant is mixed within a spray solution prior to application of sparging onto the intended dry granular material. Through the use of the adjuvant, the finished product can be applied in low light or dark light conditions through the use of mounted black light or lights ensuring precision application to the targeted area.

Now referring to FIG. 2, a comparison between dry granular materials under visible and black light shows the utility of the spray adjuvant as applied to dry granular materials. In this embodiment, as shown in FIG. 2A, the spray adjuvant is applied to a granular plant product including a bioactive agent. The spray adjuvant is mixed with the granular plant product as shown in FIG. 2B. A sample of granular plant product mixed with a photoluminescent adjuvant coating is shown in FIG. 2C under normal light and under ultraviolet light in FIG. 2D.

Example 2

Field Testing

A test of the photoluminescent adjuvant was conducted at Spring Creek Ranch Golf Club in Collierville, Tenn. at approximately 8 pm. Utilizing a 200 gallon sprayer outfitted with TEEJET 8002 nozzles at 30 psi, one (1) gallon of the photoluminescent adjuvant was added to 100 gallons of water. The mixture was under constant mechanical agitation throughout the spraying operation. With the use of an ULTRAVIOLET-150 (150 Watt) an ultraviolet black light from Altman Lighting Co. Inc., 57 Alexander Street Yonkers, N.Y. 10701, the spray operation was conducted on the 4$^{th}$ fairway. The Altman ULTRAVIOLET-150 is a compact, high-output black-light, designed to provide high-intensity illumination of fluorescent materials at distances of up to 40 feet. The fixture is sealed and designed for wet locations, and does not require any fans for cooling, resulting in extremely quiet operation. The electronic ballast was integrated into the housing. The unit was wired with 14/3 Hi-Temp rubber cable, and was supplied with a clear safety lens. The sprayer was configured for normal operations with a ten (10) foot spray boom (length) and boom height of twenty (20") inches above ground level. An initial spray pass was made from a designated starting point to a fifty (50') foot stopping point under total darkness. The sprayer changed directions to line up with the left edge (west) of the initial pass in order to ensure proper spray coverage without overlap or skip of the mixture to the target. The ULTRAVIOLET-150 was turned on prior to the advancement of the sprayer in order to line up for the second pass. The initial pass was illuminated under the black light so much so that the second pass was easily lined up for and the second pass was accurately applied to the targeted area. Under UV light, the adjuvant allowed the operator precise control of the spray mixture and showed nozzle performance across the boom better than in traditional daylight operations with spray dye indicators.

In an alternative embodiment, the photoluminescent adjuvant is made of a quinine based solution containing vitamin A and $B_{12}$ and an extracted chlorophyllic resin. The range of inclusion of each component is: quinine 1-5% w/w, vitamin A 0-1% w/w, vitamin B 0-1% w/w and chlorophyllic resin 2-5% w/w. In this experiment, the chlorophyllic resin was mechanically extracted ryegrass. Chlorophyll is activated by light and has been shown to be activated by artificial light (other than natural sunlight sources), continuing photosynthesis operations within plants, when it experiences low light or no light is important for the health of the plant. Photosynthesis has the primary task of capturing sunlight through it chlorophyll molecules and processes it with the end result being the manufacture of glucose and fructose sugars or carbohydrates for the plant to utilize as food source during its lifespan. Additionally, by absorption of the adjuvant within the tissues of the plant, the product remains active in the plant. Upon its activation in low or dark light through black light, emanation of captured "glow" light allows for the continuation of chlorophyll activation thereby increasing photosynthesis within the plant when it otherwise be photosynthetically idle at night-time.

In another embodiment the use of phosphorescent materials for foliar applications is for the absorption by plants within their tissues allowing for the plant to collect sunlight and upon activation continue the process of photosynthesis in low light or dark light conditions through emanations of stored light.

The present invention relates to the controlled delivery of chemicals, pesticides, nutrients, biostimulants, water solubles, wetting agents and water to plants with the incorporation of a phosphorescent product specifically designed for plant tissue absorption.

It is the art of this invention that allows for this adjuvant to be mixed with chemicals, pesticides, nutrients, biostimulants, water solubles, wetting agents and water to plant parts or its soil. It is the unique nature of this formulation that allows for the absorption into plant tissues for its intended purpose(s).

The adjuvant is made of a quinine based solution containing vitamins A and $B_{12}$ and an extracted chlorophyllic resin.

The adjuvant is mixed within a spray solution prior to application of the intended target. Through the use of the adjuvant total solution can be applied in low light or dark light conditions through the use of mounted black light or lights ensuring precision spray to the targeted area.

Additionally, by absorption of the adjuvant foliarly within the tissues of the plant, the product remains active in the plant and collects sunlight during daylight. Upon its activation in low or dark light, the emanation of captured "glow" light allows for the continuation of chlorophyll activation thereby increasing photosynthesis within the plant when it otherwise be photosynthetically idle at night-time.

Chlorophyll is activated by light and has been shown to be activated by artificial light (other than natural sunlight) sources. Continuing photosynthesis operations within a plant when it experiences low light or no light is important for the health of the plant. Photosynthesis has the primary task of capturing sunlight through its chlorophyll molecules and processes it with the end result being the manufacture of glucose and fructose sugars or carbohydrates for the plant to utilize as a food source during its lifespan.

These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of preferred embodiments of the invention, and are not restrictive of the invention, as claimed.

The invention claimed is:

1. A method to assist placement of a liquid based active ingredient during night-time spray operations:
    mixing a nontoxic photoluminescent product with a liquid based active ingredient to form a solution; applying said solution to targeted crops, plants and soil; providing a source of black light to illuminate said photoluminescent product and illuminating said night-time spray operations to assist in the placement of said liquid based active ingredient.

2. The method of claim 1 wherein said nontoxic photoluminescent product is an optical brightener.

3. The method of claim 1 wherein said source of said black light is mounted on a mobile apparatus to dispense the liquid based active ingredient.

4. The method of claim 1 wherein the photoluminescent product is mixed with a surfactant, to form a solubilized product.

5. The method of claim 4 wherein said solubilized product is under pressure.

6. The method of claim 5 wherein said solubilized product forms a foam when not under pressure.

7. The method of claim 1 further mixing 1-5% w/w quinine, 0-1% w/w vitamin A, 01-% w/w vitamin B and 2-5% chlorophyllic resin with said solution prior to applying said solution to targeted crops, plants and soil.

* * * * *